United States Patent [19]

Kasevich et al.

[11] Patent Number: 4,612,940
[45] Date of Patent: Sep. 23, 1986

[54] MICROWAVE DIPOLE PROBE FOR IN VIVO LOCALIZED HYPERTHERMIA

[75] Inventors: Raymond S. Kasevich, Weston; Arthur S. Dwyer, Braintree; Bart G. Guerreri, Framingham, all of Mass.

[73] Assignee: SCD Incorporated, Westborough, Mass.

[21] Appl. No.: 608,565

[22] Filed: May 9, 1984

[51] Int. Cl.[4] ............................................. A61N 5/02
[52] U.S. Cl. ............................... 128/804; 219/10.55 F
[58] Field of Search ................. 128/804; 219/10.55 R, 219/10.55 A, 10.55 F

[56] References Cited

U.S. PATENT DOCUMENTS

| 3,824,718 | 7/1974 | Nekrasov et al. | 219/10.55 R X |
|---|---|---|---|
| 4,197,860 | 4/1980 | Sterzer | 128/804 |
| 4,311,154 | 1/1982 | Sterzer et al. | 128/804 |
| 4,378,806 | 4/1983 | Henley-Cohn | 128/804 |
| 4,392,039 | 7/1983 | Risman | 219/10.55 A |
| 4,434,341 | 2/1984 | Busby | 219/10.55 R X |
| 4,446,874 | 5/1984 | Vaguine | 128/804 |
| 4,528,991 | 7/1985 | Dittmar et al. | 128/804 |

FOREIGN PATENT DOCUMENTS 2105201  3/1983  United Kingdom ................ 128/804

OTHER PUBLICATIONS

Silver; "Microwave Antenna Theory and Design", Ch. 8, pp. 239-242.
Mendecki et al.; "Microwave Applicators for Localized Hyperthermia Treatment of Cancer of the Prostate"; Radiation Oncology, 11-1980, vol. 6, No. 11.
Mendecki et al.; "Microwave Induced Hyperthermia in Cancer Treatment: Apparatus and Prelim. Results"; Int. J. Radiation Oncol. Biol. Phys., vol. 4, No. 11-12, 11-1978, pp. 1095-1103.

Primary Examiner—William E. Kamm
Assistant Examiner—Angela D. Sykes
Attorney, Agent, or Firm—Joseph S. Iandiorio; William E. Noonan

[57] ABSTRACT

A microwave dipole probe for in vivo localized hyperthermia includes an outer conductor and an inner conductor extending through and beyond the outer conductor. The portion of the inner conductor extending beyond the outer conductor is expanded in diameter relative to the portion within the outer conductor. A dielectrically loaded phase reversal sleeve is folded over the outside of the outer conductor and contains a dielectric loading material similar to the dielectric constant of the in vivo target volume.

23 Claims, 13 Drawing Figures

MICROWAVE DIPOLE PROBE FOR IN VIVO LOCALIZED HYPERTHERMIA

FIELD OF INVENTION

This invention relates to a microwave dipole probe for in vivo localized hyperthermia in cancer therapy, arterial plaque removal and melting gall and kidney stones, and more particularly to such a probe which includes fiber optics for viewing and temperature sensing.

BACKGROUND OF INVENTION

Hyperthermia at temperatures above 41° C., has been used sporadically as an agent for cancer therapy since the early 1900's. However, interest was not sustained because the results were inconsistent. More recently, results of studies of cell cultures in animals as well as some preliminary clinical trials, have revived the interest in the use of hyperthermia in cancer treatment. It is known that hyperthermia at temperatures above 41° C. kills mammalian cells and sensitizes them to ionizing radiation. It also selectively kills and radiosensitizes cells that are relatively resistant to ionizing radiation and may eliminate or reduce recovery from sublethal and potentially lethal radiation damage. The toxicity of electron affinic compounds for oxygen deficient cells and the toxicity of several chemotherapeutic agents can also be enhanced greatly by hyperthermia. There is also evidence that hyperthermia may improve the therapeutic efficacy of radiation and chemotherapeutic agents used in therapeutic practice. Hyperthermia has been applied by fluid immersion, irrigation, regional profusion, and electromagnetic waves. Radio waves, or microwaves, appear to be the most practical and efficient means for producing localized hyperthermia. In this approach electromagnetic energy is introduced into the tissue by a field that causes oscillation of ions in the tissue or changes in the electric dipole orientation of molecules, which is then locally converted into heat.

Recently, investigations into the feasibility of using small microwave antennas or probes as a means of producing local hyperthermia in cancer therapy have employed cylindrical antennas which are inserted into the body through the esophagus or rectum, or directly into a tumor using a hypodermic needle. In most cases the antenna probe is a quarter wavelength monopole antenna with frequencies in the 500 MHz to 3 GHz range. Theoretical and experimental information indicates that a single invasive microwave antenna may be used to heat tumors of a centimeter or so in diameter to therapeutically useful levels. Multiple antennas have also been used for larger tumors. These monopole antenna probes suffer from a number of shortcomings, including poor impedance matching with the target volume of the body; high senstivity to changes in the length of penetration of the probe into the body; poor uniformity in electric field and heating patterns produced; lack of beam steering, heat sensing and visual inspection capabilities. J. W. Strohbehn, et al., "An Invasive Microwave Antenna for Locally-Induced Hyperthhermia for Cancer Therapy", *Journal of Microwave Power*, 14 (4), 1979, pages 339-350; D. C. deSieyes, et al., "Optimization of an Invasive Microwave Antenna for Local Hyperthermia Treatment of Cancer", Thayer School of Engineering, Dartmouth College, July 7, 1980; J. W. Strohbehn, et al., "Evaluation of an Invasive Microwave Antenna System for Heating Deep-Seated Tumors", presented at the Third International Symposium: Cancer Therapy by Hyperthermia, Drugs and Radiation, Fort Collins, Colo., June 22-26, 1980.

SUMMARY OF INVENTION

It is therefore an object of this invention to provide an improved microwave dipole probe for in vivo localized hyperthermia.

It is a further object of this invention to provide such a microwave dipole probe which has a more uniform pattern of temperature distribution along the dipole probe.

It is a further object of this invention to provide such a microwave dipole probe in which the heating effects are confined to the dipole probe length, without secondary heating effects along the feed line away from the dipole due to antenna currents flowing along the antenna feed line.

It is a further object of this invention to provide such a microwave dipole probe which does not require a transformer or matching network between the probe and antenna feed line.

It is a further object of this invention to provide such a microwave dipole probe in which the power requirements and heating performance of the probe are independent of antenna feed line length inside the body being treated.

It is a further object of this invention to provide such a microwave dipole probe whose impedance is less sensitive to changes in frequency.

It is a further object of this invention to provide such a microwave dipole probe in which the field intensity fall-off is less severe.

It is a further object of this invention to provide such a microwave dipole probe which is less sensitive to the variations in the target volume electrical properties.

It is a further object of this invention to provide such a microwave dipole probe whose heating pattern may be varied as a function of frequency to enable longitudinal beam steering.

It is a further object of this invention to provide such a microwave dipole probe which employs fiber optic visual access to the target volume.

It is a further object of this invention to provide such a microwave dipole probe which employs fiber optic heat sensing of the target volume.

The invention results from the realization that a truly effective microwave dipole probe for in vivo localized hyperthermia can be made by expanding the size of the inner conductor beyond its exit from the outer conductor and folding back the outer conductor to form a sleeve containing a medium whose dielectric constant is close to that of the surrounding target volume.

The invention features a microwave dipole probe for in vivo localized hyperthermia. The probe includes an outer conductor and an inner conductor. The inner conductor is contained within and extends beyond the outer conductor. The portion of the inner conductor which extends beyond the outer conductor is expanded in diameter relative to the portion that is within the outer conductor. There is a dielectrically loaded phase reversal sleeve folded over the outside of the outer conductor and containing a dielectric loading material which makes the phase velocity of the current inside the sleeve match the phase velocity of the antenna current.

In a preferred embodiment the expanded inner conductor may terminate in a re-entrant microwave cavity for controlling the heating pattern in response to variations in excitation frequency. A fiber optic bundle may be disposed between the inner and outer conductors to provide visual and heat-sensing access to the target volume through the probe. The microwave dipole probe for in vivo dielectric hyperthermia may be used in groups of two or more to form a multi-probe phased array.

The expanded inner conductor may be approximately equal in length to the outer conductor. The dielectric loading material will have a dielectric constant and electrical conductivity nearly the same as that of the in vivo target volume. The dielectric loading material may be a polyester resin composition. The probe length may be approximately one half wavelength. The re-entrant microwave cavity may include a dielectric loading material and the fiber optic bundle may terminate proximate the end of the outer conductor or extend into the expanded center conductor. There may be means for transmitting and receiving visible light radiation laterally from the probe between the surrounding target volume and the terminus of the fiber optic bundle. The means for transmitting and receiving may include simply the polished ends of the fibers. It may also include a reflecting surface. The inner conductor may be interconnected with the expanded inner conductor by a transition section, and that transition section may include the reflecting surface. The gap between the outer conductor and the expanded inner conductor may be dielectrically loaded. The fiber optic bundles may include at least one optical fiber for transmitting radiation to the target volume and at least one optical fiber for receiving radiation to the target volume. There may be a heat-sensitive optical load whose reflection coefficient changes with temperature at the terminus of one or more of the optical fibers for modifying transmitted radiation as a function of the temperature of the surrounding target volume. The received radiation would be compared to the reflected radiation to determine temperature. There may be a fluorescent load emitting visible light whose spectrum changes with temperature. The remote sensing of two visible emission lines and taking their ratio provides an accurate temperature measurement of the target volume adjacent to the probe. The outer conductor may be a metallic coating formed on the external surface of the fiber optic bundle. The probe may be entirely covered with a dielectric material.

DISCLOSURE OF PREFERRED EMBODIMENT

Other objects, features and advantages will occur from the following description of a preferred embodiment and the accompanying drawings, in which.

Figure 1:
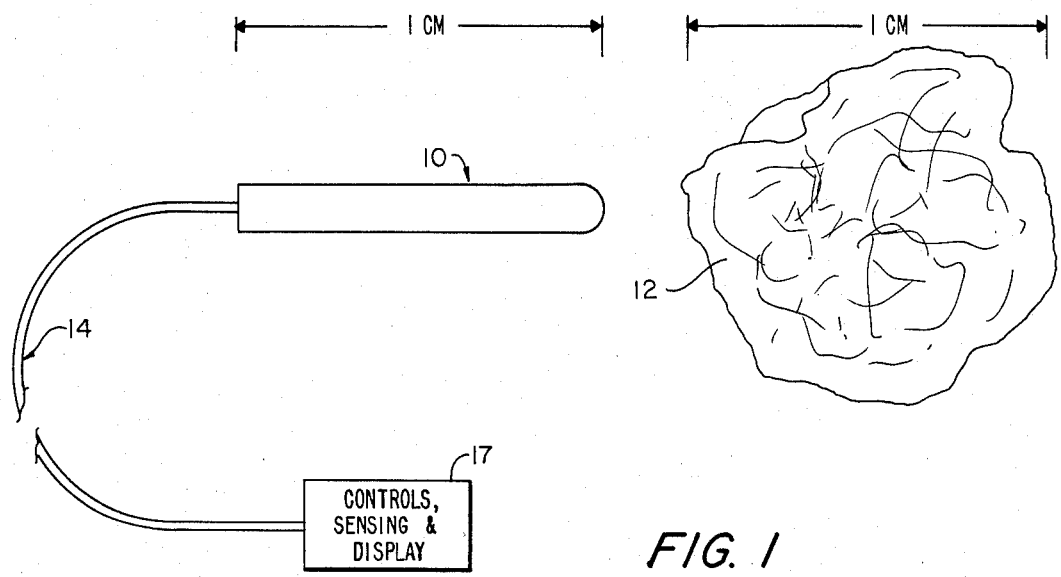
FIG. 1 is an illustration of the probe according to this invention with control circuits and a typical target volume, or tumor.

The invention may be accomplished with a microwave dipole probe for in vivo localized hyperthermia, which includes an outer conductor and inner conductor extending into and beyond the outer conductor. A portion of the inner conductor extends beyond the outer conductor and is expanded relative to the portion within the outer conductor. A dielectrically loaded phase reversal sleeve is folded over the outside of the outer conductor and contains a dielectric loading material similar to the dielectric constant of the in vivo target volume. The microwave electric fields supplied by the probe may be in the frequency range of 500 MHz to 10 GHz so that the electric field my be selected at a frequency where the absorption rate of the particular target volume may be several times that of surrounding healthy tissue. In addition to attacking cancerous tumors, the probe may be used for other in vivo hyperthermia therapies, such as the reduction of plaque in arteries and breaking up of gall and kidney stones. With this improved probe, the spatial fall-off of the temperature beyond the target volume is very steep. By the use of the sleeve with the dielectric medium, radiation is confined to the region of the probe and does not extend back up the outside of the antenna feed line. The addition of a re-entrant cavity provides a capability for vertical beam steering by frequency adjustment. A typical beam pattern provides maximum radiated power at right angles to the longitudinal axis of the probe. A multi-probe arrangement may be positioned in spaced locations around the target volume to provide directional radiation patterns. In addition, the radiation from each of the probes in a multi-probe structure may be excited in current phased relationship with one another so that the fields subtract in some areas and add in others. In addition, the temperature distribution patterns may be continuously varied in time by changing the relative phasing of the probes. The radiated power may be pulsed or continuous.

Visual inspection of a cancer tumor or other target volume may be accomplished by means of fiber optics integrally formed with the microwave probe. The inner conductor may be formed at the center of the fiber optic bundle, and the outer conductor may be formed as a cylinder surrounding the fiber optic bundle or may be a metal coating such as a nickel alloy vapor-deposited or sputtered onto the outside of the fiber optic bundle. The fiber optic bundle may be used to illuminate the target volume and return the reflected light from it to the fibers to a viewing and display device. Each return fiber may be terminated in a refractive index lens for expanded viewing and display. A thin-wall glass coating or cover may be provided over the entire body of the dipole to protect it from body fluids and to enhance its isolation from the electrical properties of the body. It also provides a viewing window for optical radiation fields. A heat-sensitive optical load, such as a gallium arsenide semiconductor, may be placed at the terminus of optical fibers proximate the tumor. Such devices change their reflection coefficient with temperature so that the difference between incident and reflected light on the gallium arsenide crystal semiconductor can be calibrated to changes in temperature of the target volume. There may be a fluorescent load emitting visible light whose spectrum changes with temperature. The remote sensing of two visible emission lines and taking their ratio provides an accurate temperature measurement of the target volume adjacent to the probe. Dino Paporitis, "Keeping the Heat on Cancer", Photonics Spectra, March 1984, Vol. 18, Issue 3, p. 53.

Figure 2:
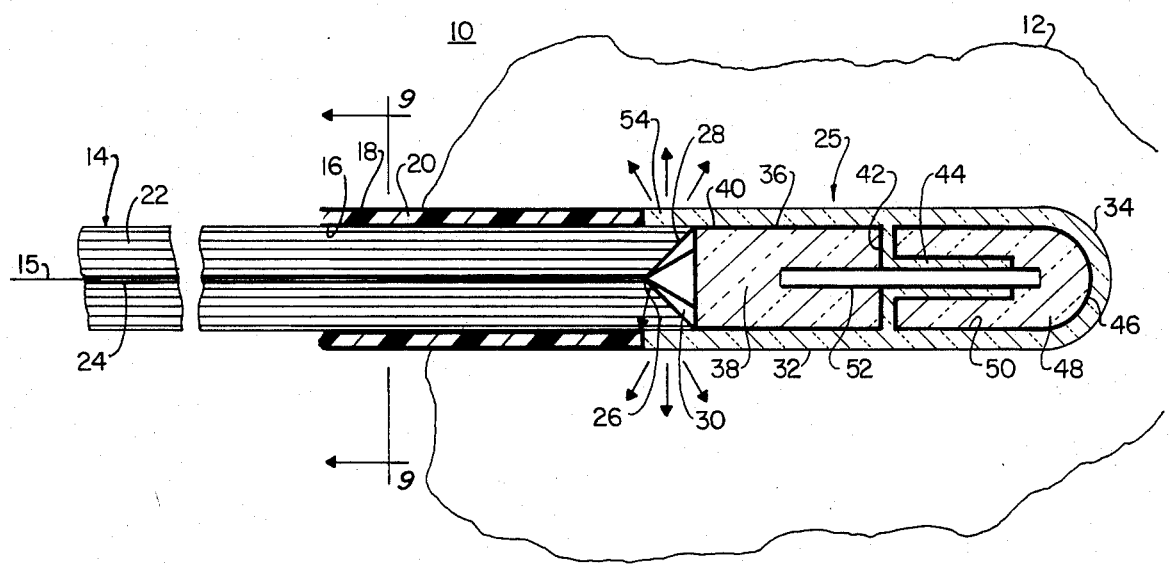
FIG. 2 is a cross-sectional view of the probe of FIG. 1.

A microwave dipole probe 10 according to this invention is shown in FIG. 1, juxtaposed to a target volume 12 which may be a cancer tumor. Probe 10 is connected by a coaxial antenna feed line 14 to suitable control sensing and display circuits 17. Probe 10, FIG. 2, is longitudinally symmetrical about longitudinal axis 15 and is generally tubular in form. It is approximately one centimeter in length or longer, depending on the tumor site, and includes an outer conductor 16, which is formed of a metal such as a nickel alloy as an extension of the outer conductor of antenna feed coaxial line 14. Outer conductor 16 is folded over on itself to form a phase reversal sleeve 18 which is filled with a dielectric 20 having a dielectric constant which is similar to that of the surrounding target volume. Typically the dielectric may be polyester resin composition, with a dielectric constant of $\Sigma_r=40$. Fiber optic bundle 22 is contained between outer conductor 16 and inner conductor 24 in coaxial cable antenna feed 14 and in probe 10. Beyond the end of outer conductor 16, inner conductor 24 expands, 25. Inner conductor 24 is connected to the apex 26 of a cone, pyramid, six-sided pyramid, or the like, 28, whose surface is metallically coated such as with a chromium or nickel alloy and constitutes the transition portion 30 of the inner conductor between the single line form 24 within outer conductor 16 and the expanded form 25 beyond the end of outer conductor 16. A cover 32, formed of a dielectric material such as glass, extends from the end of outer conductor 16 to the rounded distal end of the probe 34. The expanded inner conductor 25 is formed by a metallic cylindrical coating 36 plated on, for example, a glass cylinder 38 disposed in chamber 40. The metal coating 36 in contact with the metal surface 30 of pyramid 28 forms the continuous expanded inner conductor 25. The expanded inner conductor 25 continues along the end of cylinder 42, on the outside surface of re-entrant cavity 44 and on the surface 46 of glass plug 48 in forward chamber 50. A glass or other dielectric pin 52 may be used to hold together plug 48 and cylinder 38. The gap 54 between the end of outer conductor 16 and the expanded outer conductor 60 25 may be left open as much as structually possible if contamination by body fluids is not a problem. If it is, then the gap will be covered typically by the same dielectric, such as glass, which is used to form insulating cover 32. To accommodate the emission and reception of radiation by the fiber optic bundle 22, gap 54 may be at least partially formed of transparent glass material. Fibers may continue across the gap and enter into the expanded center conductor by means of holes in the reflecting surface. Light fed down some of the fibers of fiber optic bundle 22 reflects off the metallic surface 30, which also functions as an optical reflecting surface, to illuminate the surrounding target volume. Reflected radiation is received by others of the optical fibers and transmitted back to external equipment for display.

Figure 2A:
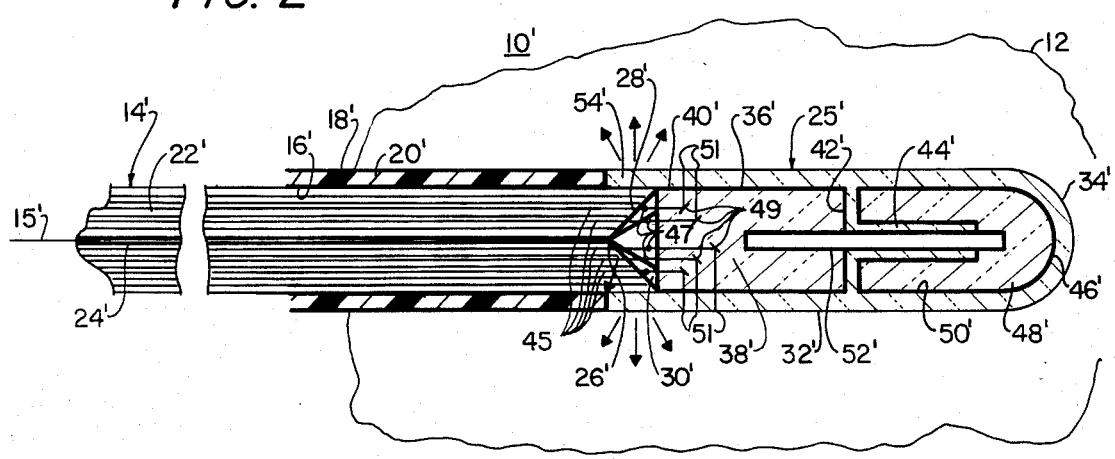
FIG. 2A is a cross-sectional view of the probe of FIG. 1 similar to that shown in FIG. 2 with a fiber optic extended into the expanded center conductor.

Probe 10', FIG. 2A, is similar to that shown in FIG. 2, but certain elements 45 of the fiber optic bundle 22' are extended through holes 47 in reflecting surface 30' without disturbing the general reflecting property of the surface and into cylinder 38' provided with mirrors 49 to redirect the light laterally out of ports 51 in the expanded conductor 25'. Instead of mirrors the elements 45 could be simply bent to redirect the light.

Figure 3:
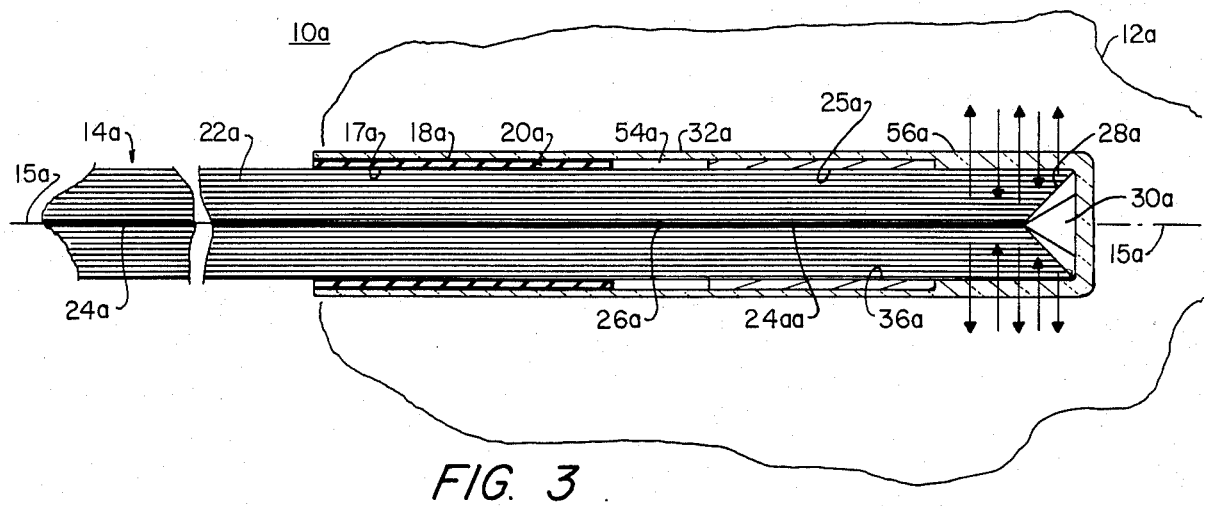
FIG. 3 is a cross-sectional view of an alternative probe similar to that of FIG. 2.

In probe 10a, FIG. 3, inner conductor 24a begins to expand generally in the area of 26a to form expanded inner conductor 25a by virtue of the capacitive coupling between the extended inner conductor 24aa and the surrounding cylindrical surface 36a which is capacitively coupled to it. The expanded inner conductor 24a continues with the surface of metallic coating 30a coated on pyramidical member 28a, which in this case does not function as a transition section as it did in probe 10, FIG. 2. However, the pyramidical section 30a does act as a reflecting member by virtue of the polished nature of the metallic surface 28a. A dielectric cover 32a is typically made of transparent glass in the area 56a where radiation must be emitted and returned through the ends of the fiber optic elements via reflecting surface 28a. However, in gap 54a the insulating dielectric cover 32a need not be transparent, for that no longer is used as the viewing port. As shown in FIG. 3, cover 32a may extend over the entire probe including outer conductor 17a and sleeve 18a.

Figure 4:
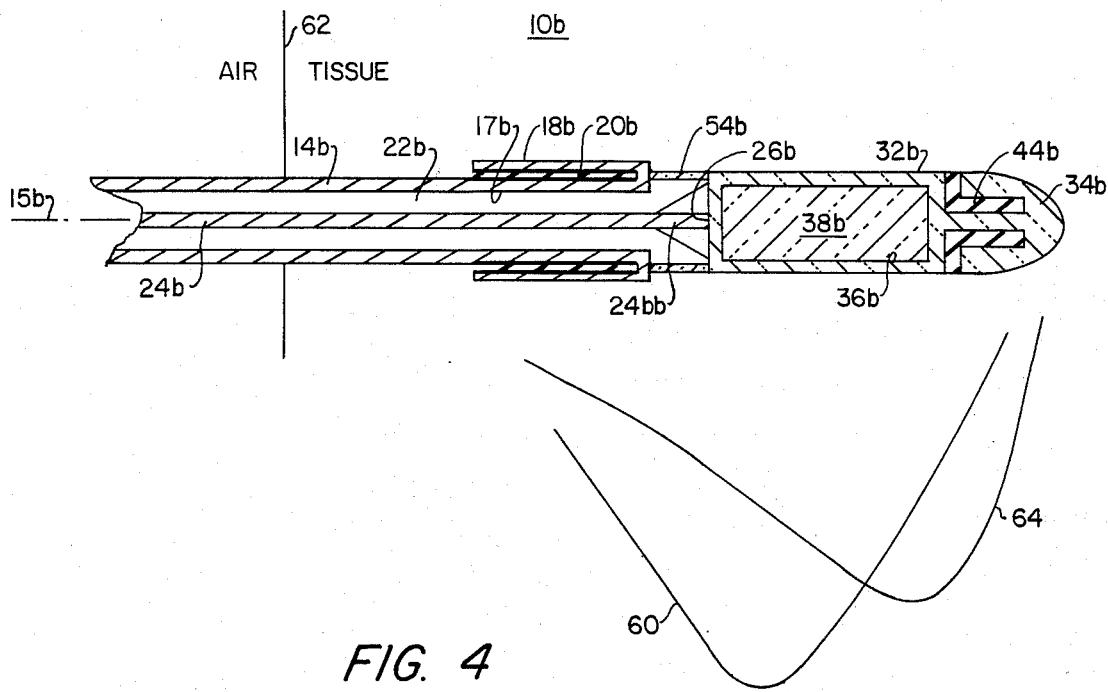
FIG. 4 is a cross-sectional view of another alternative construction of a probe similar to that shown in FIG. 2, illustrating the steerable heating pattern.

In an alternative construction, FIG. 4, extension 24bb of inner conductor 24b transitions abruptly at 26b into the expanded inner conductor 36b plated on the inside of chamber 38b. Because of the folded over sleeve 18b with the dielectric 20b, probe 10b has a power radiating field, and consequently a heat pattern distribution 60 which is confined to the length of the probe. That is, sleeve 18b with dielectric 20b functions as a choke or phase reversal medium to prevent leakage antenna currents from flowing on the surface of coaxial cable lead 14b and producing secondary heating effects along feed 14b. In addition to providing a more uniform and predictable pattern, it also makes the probe independent of its depth in the tissue within the body because antenna lead 14b is no longer so sensitive to the air-tissue interface 62. Longitudinal beam steering is accomplished with the presence of re-entrant cavity 44b, which is formed of a suitable dielectric such as a resin compound by varying the excitation frequency of the probe. For example, for the power absorption profile indicated at 60 an excitation frequency of 1 GHz is used. By shifting that frequency to 5 GHz, the beam may be steered to provide the power absorption profile 64.

Figure 5:
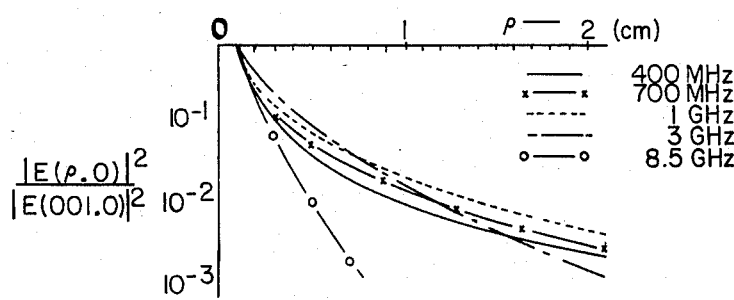
FIG. 5 is a representation of the radial fall-off in heating produced by the probe in muscle tissue at various excitation frequencies.

One advantage of the expanded inner conductor is that it reduces the electric field gradient at the surface of the dipole so that beyond its perimeter the field falls off less abruptly. This is shown in FIG. 5, where the field behavior in materials having values of dielectric constant and conductivity corresponding to muscle tissue are shown as decreasing relatively slowly close to the probe for various frequencies from 400 MHz to 8.5 GHz.

Figure 6:
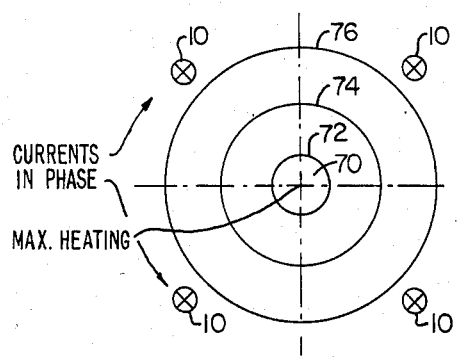
FIG. 6 is a diagram showing a circular heating pattern obtained with a multi-probe phased array.
Figure 7:
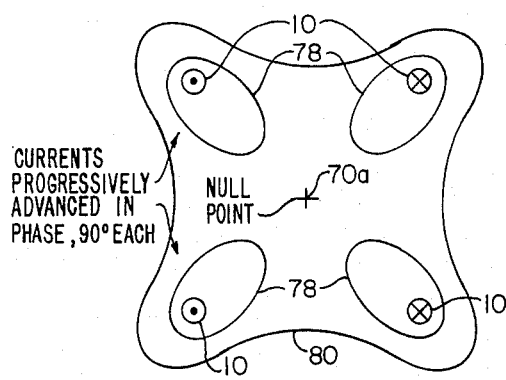
FIG. 7 is a diagram showing a cloverleaf heating pattern obtainable with a multi-probe phased array with 90° phase shift.

The probes shown in FIGS. 2, 3, and 4 may be used in a multi-probe phased array, such as shown in FIG. 6, wherein four probes are equally spaced about the maximum heating center 70 to provide a circular heating pattern which is most intense at the center and is circularly uniform, as shown by the isotherms 72, 74, 76. The currents are in phase in each of probes 10, FIG. 6. However, in FIG. 7 the currents are not in phase, but rather are progressively advanced by 90°. This creates a null point at center 70a and a cloverleaf heating pattern represented by isotherms 78 and 80.

Figure 8:
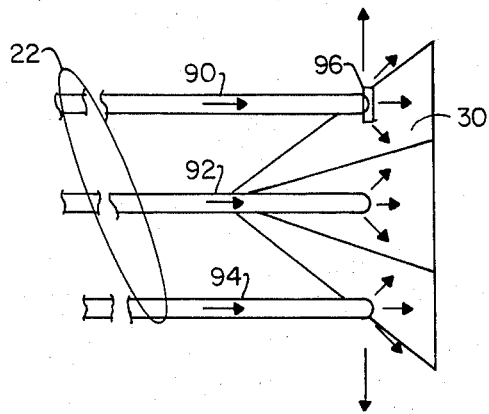
FIG. 8 is an enlarged view of the polished rounded ends of a few optical fibers in the fiber optic bundle.

Individual optical fibers 90, 92, 94, FIG. 8, in fiber optic bundle 22 may have polished rounded ends to enhance their distribution and reception of the light. One or more of the fiber optic rods may include at its terminus a heat-sensitive load, such as a gallium arsenide semiconductor 96, whose reflection coefficient changes with changes in temperature. Thus light directed down fiber 90 is differently affected when it strikes the surface of semiconductor 96 depending upon the temperature of semiconductor 96. These differences can be detected in the reflected light by suitable equipment and the control sensing and display 17, FIG. 1.

Figure 9:
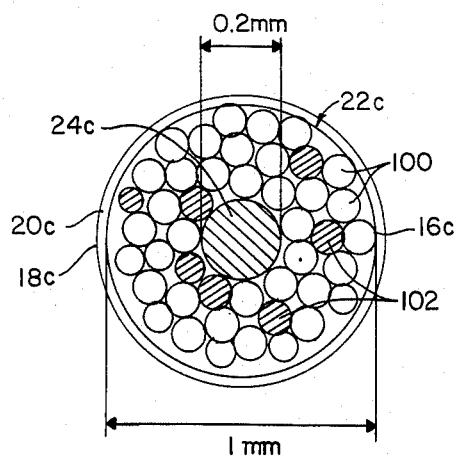
FIG. 9 shows a cross-section through the fiber optic bundle taken along line 9—9 of FIG. 2.
Figure 10:
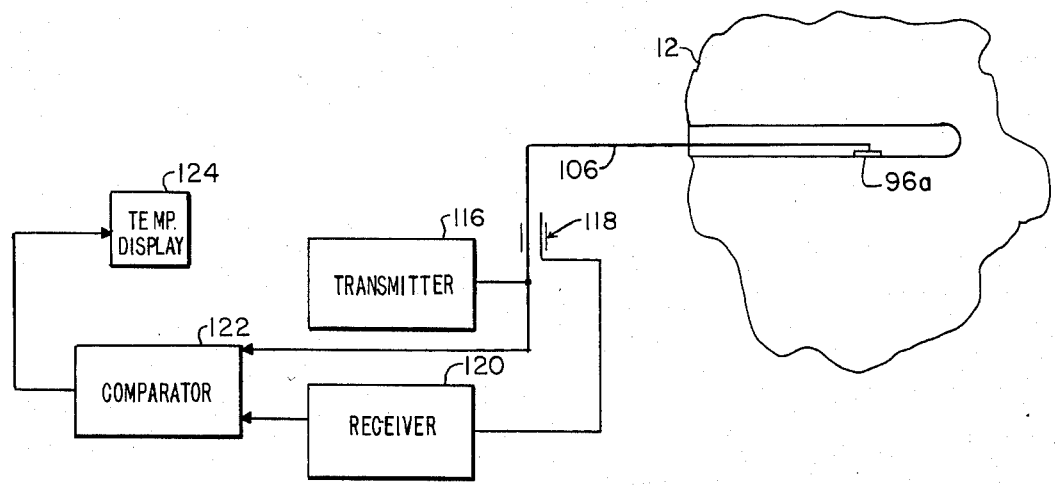
FIG. 10 is a block diagram showing two different temperature sensing techniques usable with the probe of this invention.
Figure 11:
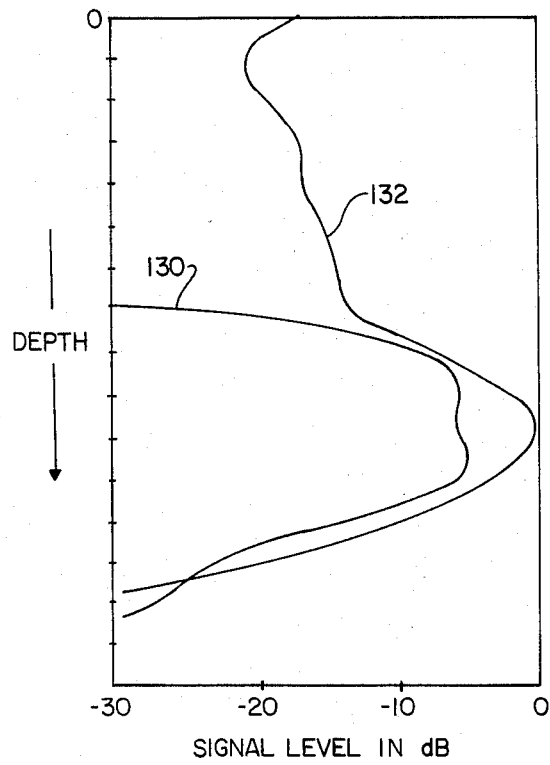
FIG. 11 is a diagram showing the broader band, more uniform field distribution of the probe according to this invention.

Fiber optic bundle 22c, FIG. 9, is composed of a number of optical fibers surrounding inner conductor 24c. Some of those optical fibers are light-transmitting, 100; some of them are light-receiving, 102. Typically, the center conductor is approximately 0.2 mm in diameter and the entire optical bundle, including the vapor-deposited or sputtered metallic clad 16c, has an overall diameter of approximately 1 mm. to 2 mm. Temperature determination using a heat-sensitive optical load, such as a gallium arsenide semiconductor 96a, FIG. 10, is constructed using a fiber optic element 106 which receives light from light transmitter 116 and delivers it to the surface semiconductor 96a, whose reflection coefficient varies with temperature. The reflected light is tapped through passive coupler 118 to receiver 120, where it is delivered to comparator 122 in combination with the original light from transmitter 116. The determined temperature is then displayed in temperature display 124. The broad-band, uniform nature of the signal produced by the probe of this invention is shown by characteristic 130, FIG. 11, presented for comparison with a similar characteristic 132 for typical conventional monopole probes.

Other embodiments will occur to those skilled in the art and are within the following claims:

What is claimed is:

1. A microwave dipole probe for localized hyperthermia of an in vivo target volume, comprising:
    an outer conductor;
    an inner conductor extending through and beyound said outer conductor, the portion of said inner conductor extending beyond said outer conductor being expanded in diameter relative to the portion within said outer conductor; and
    a dielectrically loaded phase reversal sleeve folded over the outside of said outer conductor and containing a dielectric loading material similar to the dielectric constant of the in vivo target volume.

2. The microwave dipole probe of claim 1 in which said expanded inner conductor is approximately equal in length to said outer conductor.

3. The microwave dipole probe of claim 1 in which said dielectric loading material has a conductivity similar to that of the in vivo target volume.

4. The microwave dipole probe of claim 1 in which said dielectric loading material is a polyester resin composition.

5. The microwave dipole probe of claim 1 in which said probe length is approximately one half wavelength at the operation frequency and several wavelengths long when undergoing longitudinal beam steering at higher frequency.

6. The microwave dipole probe of claim 1 further including a re-entrant microwave cavity means responsive to said inner conductor for controlling the heating pattern in response to variations in excitation frequency.

7. The microwave dipole probe of claim 6 in which said re-entrant microwave cavity means includes dielectric loading material.

8. The microwave dipole probe of claim 1 further including a fiber optic bundle disposed between said inner and outer conductors.

9. The microwave dipole probe of claim 8 in which said fiber optic bundle terminates proximate the end of said outer conductor and there are means for transmitting and receiving radiation laterally of said probe between the surrounding target volume and the terminus of said fiber optic bundle.

10. The microwave dipole probe of claim 9 in which said means for transmitting and receiving includes the polished ends of the fiber.

11. The microwave dipole probe of claim 9 in which said means for transmitting and receiving includes a reflecting surface.

12. The microwave dipole probe of claim 11 in which said inner conductor is interconnected with said expanded inner conductor by a transition section and said transition section includes said reflecting surface.

13. The microwave dipole prove of claim 8 in which said fiber optic bundle includes at least one optical fiber means for tramsmitting radiation to the said target volume and at least pne optical fiber means for receiving radiation from said target volume.

14. The microwave dipole probe of claim 8 in which at least some of the fiber optic elements in said fiber optic bundle extend through said reflecting surface into the expanded inner conductor.

15. The microwave dipole probe of claim 8 in which at least one of the optical fibers in said fiber optic bundle includes at its terminus a heat-sensitive optical load whose reflection coefficient changes with temperature.

16. The microwave dipole probe of claim 8 in which said outer conductor is a metallic coating on the external surface of said fiber optic bundle.

17. The microwave dipole probe of claim 1 in which said inner conductor is interconnected with said expanded inner conductor by a transition section.

18. The microwave dipole probe of claim 1 in which the gap between said outer conductor and said expanded inner conductor is dielectrically loaded.

19. The microwave dipole of claim 1 in which said probe is covered with a dielectric material.

20. A microwave dipole probe for localized hyperthermia of an in vivo target volume, comprising:
    an outer conductor;
    an inner conductor extending through and beyond said outer conductor, the portion of said inner conductor extending beyond said outer conductor being expanded in diameter relative to the portion within said outer conductor;
    a dielectrically loaded phase reversal sleeve folded over the outside of said outer conductor and containing a dielectric loading material similar to the dielectric constant of the in vivo target volume; and a re-entrant microwave cavity means responsive to said inner conductor for controlling the heating pattern in response to variations in excitation frequency.

21. A fiber optic microwave dipole probe for localized hyperthermia of an in vivo target volume, comprising:

an outer conductor;

an inner conductor extending through and beyond said outer conductor, the portion of said inner conductor extending beyond said outer conductor being expanded in diameter relative to the portion within said outer conductor;

a dielectrically loaded phase reversal sleeve folded over the outside of said outer conductor and containing a dielectric loading material similar to the dielectric constant of the in vivo target volume; and a fiber optic bundle disposed between said inner and outer conductors.

22. A fiber optic microwave dipole probe for localized hyperthermia of an in vivo target volume, comprising:

an outer conductor;

an inner conductor extending through and beyond said outer conductor, the portion of said inner conductor extending beyond said outer conductor being expanded in diameter relative to the portion within said outer conductor;

a dielectrically loaded phase reversal sleeve folded over the outside of said outer conductor and containing a dielectric loading material similar to the dielectric constant of the in vivo target volume;

a re-entrant microwave cavity means responsive to said inner conductor for controlling the heating pattern in response to variations in excitation frequency; and a fiber optic bundle disposed between said inner and outer conductors.

23. A multiprobe phased array including a number of space microwave dipole probes for localized hyperthermia of an in vivo target volume, each of which comprises:

an outer conductor;

an inner conductor extending through and beyond said outer conductor, the portion of said inner conductor extending beyond said outer conductor being expanded in diameter relative to the portion within said outer conductor; and a dielectrically loaded phase reversal sleeve folded over the outside of said outer conductor and containing a dielectric loading material similar to the dielectric constant of the in vivo target volume.

* * * * *